(12) United States Patent
Zhong

(10) Patent No.: US 8,251,931 B2
(45) Date of Patent: Aug. 28, 2012

(54) CASTING APPARATUS AND METHOD FOR USING THE SAME

(76) Inventor: Bing-Tang Zhong, Houston, TX (US)

( * ) Notice: Subject to any disclaimer, the term of this patent is extended or adjusted under 35 U.S.C. 154(b) by 0 days.

(21) Appl. No.: 12/430,890

(22) Filed: Apr. 27, 2009

(65) Prior Publication Data

US 2009/0209892 A1 Aug. 20, 2009

Related U.S. Application Data

(63) Continuation of application No. 11/740,281, filed on Apr. 25, 2007, now abandoned.

(51) Int. Cl.
*A61F 5/00* (2006.01)
*A61F 5/37* (2006.01)
(52) U.S. Cl. .......................... 602/5; 128/882
(58) Field of Classification Search ................ 602/5, 13, 602/21, 20, 19, 23; 128/882; 5/655, 911, 5/655.4, 630, 702, 632, 367, 352, 357, 91, 5/337, 338, 341
See application file for complete search history.

(56) References Cited

U.S. PATENT DOCUMENTS

| | | | | | |
|---|---|---|---|---|---|
| 3,212,497 | A | * | 10/1965 | Dickinson ........................ | 602/6 |
| 3,515,625 | A | * | 6/1970 | Mavromatis et al. ...... | 428/317.9 |
| 3,745,998 | A | * | 7/1973 | Rose ................................ | 602/6 |
| 3,762,404 | A | * | 10/1973 | Sakita ........................... | 5/655.4 |
| 4,139,920 | A | * | 2/1979 | Evans ........................... | 5/655.4 |
| 4,862,879 | A | * | 9/1989 | Coombs ........................ | 602/13 |
| 6,161,239 | A | * | 12/2000 | Grazel ........................... | 5/655 |
| 6,936,002 | B2 | * | 8/2005 | Kochamba et al. ............ | 600/37 |

* cited by examiner

*Primary Examiner* — Patricia Bianco
*Assistant Examiner* — Tarla Patel
(74) *Attorney, Agent, or Firm* — Nick A Nichols, Jr.

(57) ABSTRACT

A casting or splinting device comprises a plastic casting body formed into various configurations for immobilizing a bone fracture or the like. The casting body is filled with small spherical granules having a smooth and slippery surface. The casting body is sealed and provided with an outlet port for aspirating air from within the casting body. Aspiration of air from the casting body results in a rigid casting or splint.

9 Claims, 3 Drawing Sheets

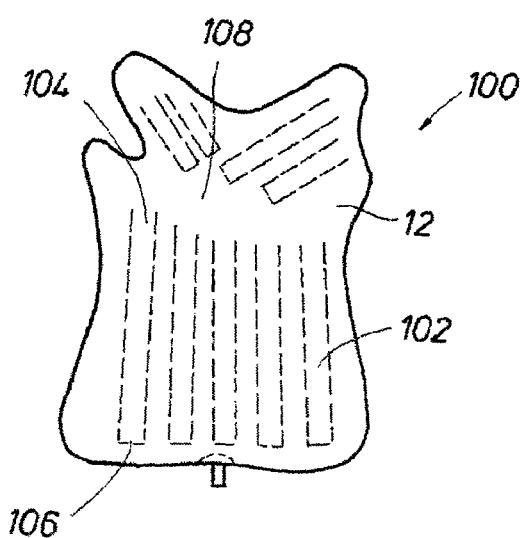
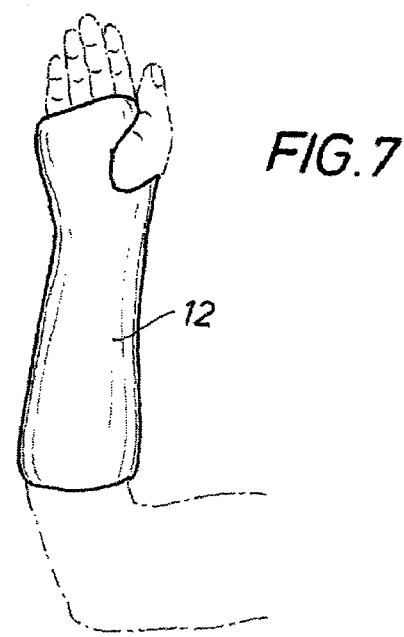
FIG. 6
FIG. 7
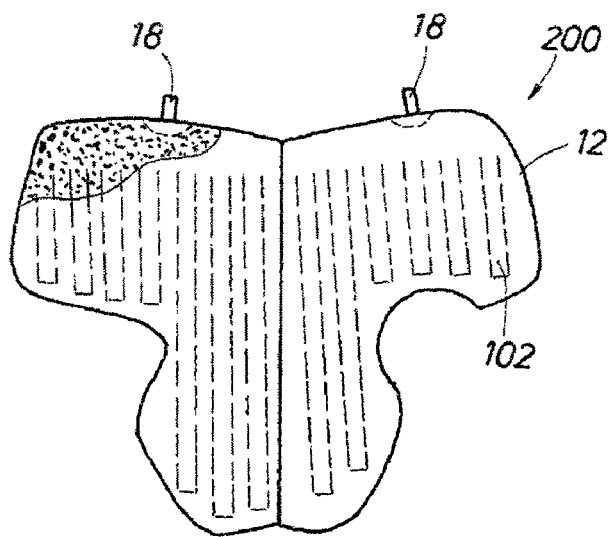
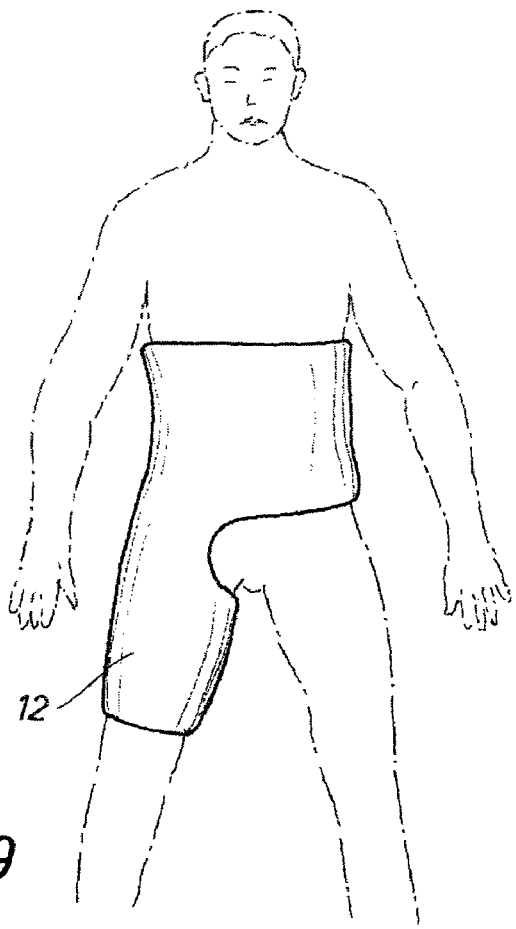
FIG. 8
FIG. 9

CASTING APPARATUS AND METHOD FOR USING THE SAME

CROSS-REFERENCE TO RELATED APPLICATION

This is a continuation of U.S. patent application Ser. No. 11/740,281, filed Apr. 25, 2007, now abandoned.

BACKGROUND OF THE INVENTION

The present invention relates generally to the field of casting material, and more particularly to the design of a casting apparatus for forming a rigid structure for application in skeletal and joint fixation.

In clinical practice, there are many conditions and circumstances, such as fractures and dislocations of bones and joints, injuries of muscles, tendons, fasciae and ligaments, correction of congenital and acquired deformities, etc., in which the involved skeletal and joint have to be fixed for treatment. Plaster of paris has been used as casting material for skeletal and joint fixation for more than one hundred years and is still the standard casting material in many countries. But it is not without drawbacks, such as heavy weight, water intolerance, etc. In recent years, synthetic resin (polyurethane resin, etc.) has been used widely and has become part of the established orthopedic practice in most developed countries. Although resin impregnated splinting bandages have many advantages over traditional based materials, they still have some drawbacks. Typically, synthetic splints are created from a resin impregnated fabric contained within a moisture impervious sleeve prior to use. In use, the resin impregnated fabric is wetted and then applied to the body part requiring a splint. A synthetic splint thus requires an activator, may irritate the skin and cause an allergic reaction. Both the plaster of paris and the synthetic resin casts require a substantial period of time for the cast to set and hardened, and require multiple step to prepare and are difficult and messy to apply. In addition, these casts are removed by cutting them off the patient and discarded and thereby adding to the pollution of the environment.

The plaster of paris and synthetic casting methods both have advantages and disadvantages. The casting material of the present invention eliminates the disadvantages of plaster of paris and synthetic resin casting material and methods but reserves all of the advantages of both. Moreover, the casting material of the present invention may be used repeatedly many times, hence there is no waste and trash to pollute the environment and energy and water are conserved by eliminating the multi step preparation process required by the plaster of paris and synthetic casting methods.

SUMMARY OF THE INVENTION

It is an object of the present invention to provide a casting apparatus that is reusable and that is easy to apply and remove.

It is further an object of the present invention to provide a casting apparatus that uses closely compressed spherical granules under atmospheric pressure to immobilize a body part.

It is yet another object of the present invention to provide a casting apparatus wherein the stiffness or hardness of the casting is adjustable by removal of air contained within the casting apparatus.

It is still another object of the present invention to provide a casting apparatus where air may be removed from within the casting with a suction pump.

In one embodiment of the present invention, a casting apparatus comprises a plastic casting body adapted for immobilizing a body limb or part. The casting body is filled with small spherical granules and is sealed about the perimeter thereof. The casting apparatus includes a nozzle opening into the casting body for aspirating air therefrom. The casting body may be shaped to conform to the shape of the immobilized body part. Upon Aspiration of air from the interior of the casting body, a hard rigid casting about the immobilized body part is formed.

In another embodiment of the present invention the casting body is divided into a plurality of compartments for more even distribution of the spherical granules therein. Portions of the casting body may be devoid of compartments or channels thereby permitting more flexibility for shaping the casting about joints or the like.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 6 is a schematic view of an alternate embodiment of the forearm pattern casting of the present invention;

FIG. 7 is a side elevation view of the forearm pattern casting shown in FIG. 6 applied to the forearm of a patient;

FIG. 8 is a schematic view of a hip spica pattern casting of the present invention;

FIG. 9 is a side elevation view of the hip spica casting of the present invention applied to the body of a patient;

DETAILED DESCRIPTION OF A PREFERRED EMBODIMENT

Figure 1:
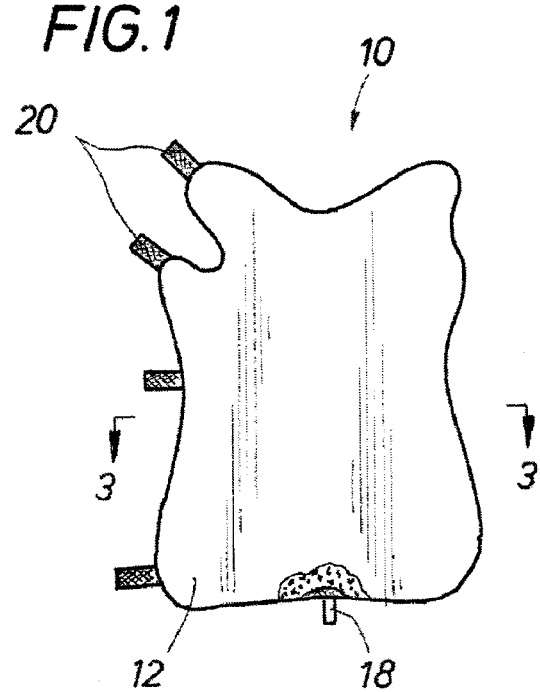
FIG. 1 is a schematic view of a forearm pattern casting of the present invention.

Referring first to FIG. 1, an embodiment of the invention is generally identified by the reference numeral 10. The casting apparatus 10 defines a casting body 12 adapted for application about the forearm of a patient. The casting body 12 is fabricated of a soft, air-tight plastic or latex material filled with hard non-deformable spherical plastic granules 14. The granules 14 have an average diameter of 1-2 mm and the surface thereof is smooth and slippery.

Figure 3:
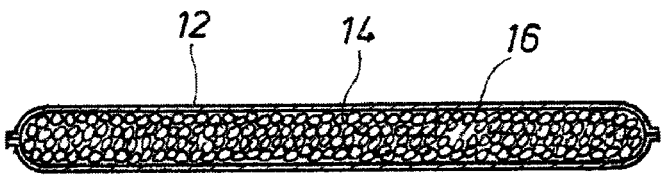
FIG. 3 is a section view of the forearm pattern casting of the present invention taken along line 3-3 of FIG. 1.
Figure 4:
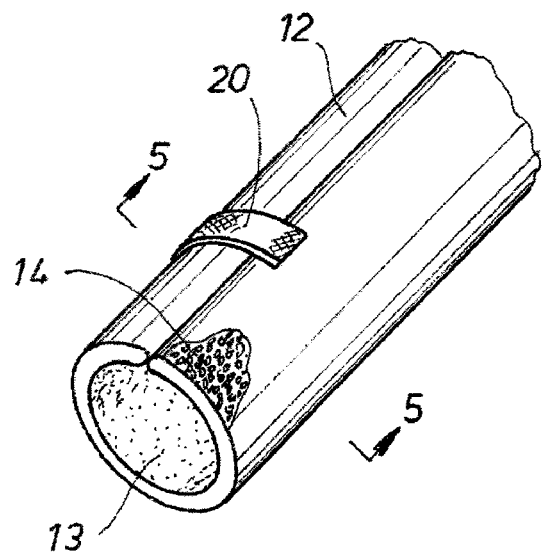
FIG. 4 is perspective view of the forearm pattern casting of the present invention.
Figure 5:
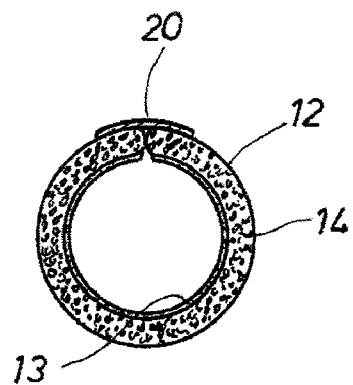
FIG. 5 is a section view of the forearm pattern casting of the present invention taken along line 5-5 of FIG. 4.

Referring now to FIGS. 1 and 3, the casting body 12 comprises a unitary body of plastic material that when laid flat includes substantially planar top and bottom surfaces sealed about the perimeter thereof. The top and bottom surfaces of the casting body 12 are spaced apart to form a relatively narrow longitudinal cavity 16 containing the granules 14. The surface of the casting body 12 that will contact the patient's skin is lined with a layer 13 of felt, cotton material or the like so as not to irritate the patient's skin. The casting body 12 further includes a nozzle 18 providing fluid access to the cavity 16. The nozzle 18 is internally threaded for connecting the casting apparatus 10 to a suction pump or other device for removal of air from within the casting body 12. The opposite end of the nozzle 18 (open to the cavity 16) is provided with a screen or slotted plug that permits air to be aspirated out of the cavity 16 but prevents the spherical granules 14 from being drawn into and plugging the nozzle 18.

Figure 2:
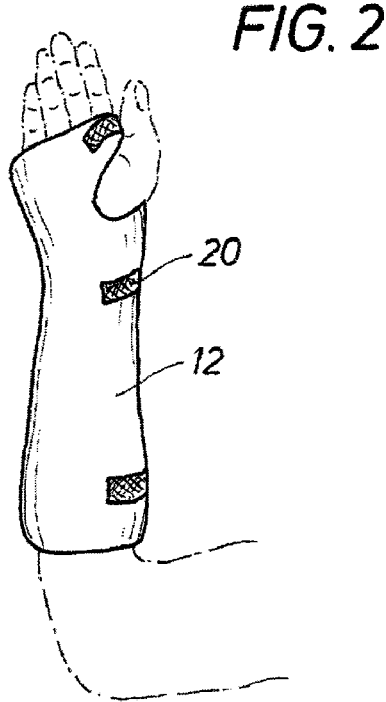
FIG. 2 is a side elevation view of the forearm pattern casting applied to the forearm of a patient.

As shown in FIG. 1, the casting body 12 is relatively flat and may be manipulated to wrap around a patient's body member which may need to be immobilized. Specifically, the casting body 12 depicted in FIG. 1 defines a pattern or configuration for wrapping about a patient's forearm, as best shown in FIG. 2.

The casting body 12 is applied about the patient's forearm and the nozzle 18 is connected to a vacuum pump or similar suction device. The casting body 12 is wrapped about the patient's forearm and shaped to conform to the contour and shape of the patient's forearm. The longitudinal sides of casting body 12 are brought into facing contact so that the casting body 12 fully encircles the patient's forearm. Straps 20, such as Velcro straps, attached to the outer surface of the casting body 12 are secured to retain the casting apparatus about the patient's forearm. Air is then aspirated from the cavity 16 and the casting body 12 immediately hardens and aspiration of air is ceased. The casting body 12 becomes rigid and hard within a few seconds, typically within five seconds, of beginning to aspirate air out of the body cavity 16. The suction pump is disconnected and a plug is threaded into the nozzle 18 and a clip or the like is secured about the stem of the nozzle 14 thereby preventing entry of air into the cavity 16. The casting body 12 is now a hard and rigid cast about the patient's forearm.

Aspiration of air from the casting body 12 and the external force of atmospheric pressure compress the spherical granules 14 against each other, The smaller granules 14 slip about and fill in the gaps or spaces between the larger granules 14. As the air is removed from the casting body 12, the granules 14 become more tightly packed to form the casting body 12 into a hard rigid cast or mold to the desired shape. This shape is maintained so long as air is not permitted to enter the casting body 12. The degree of rigidity or hardness of the casting body 12 may be adjusted by controlling the volume of air aspirated out of the casting body 12 so that it is easy to manipulate.

The cast 10 may be easily removed by undoing the Velcro straps 20 and opening the nozzle 18. The entry of air into the cavity 16 of the casting body 12 immediately relaxes the casting body 12 and the stiffness thereof is no longer maintained. The casting apparatus 10 may then be stored and used again and again thereby eliminating waste and trash that would contribute to pollution of the environment.

Referring now to FIG. 6, an alternate embodiment of the present invention is generally identified by the reference numeral 100. The cast 100 is substantially the same as the cast 10 described above with the exception that cavity 16 of the cast 100 is divided into a plurality of compartments or channels 102. The channels 102 are open at one end 104 and closed at the opposite end 106 thereof. The channels 102 permit more even distribution of the granules 14 throughout the cavity 16 of the casting body 12 and upon aspiration of air from the casting body 12 function like solid rods to maintain the shape of the cast 100. The cast 100 may also be provided with two or more nozzles 18 to more quickly aspirate air from the casting body 12.

Figure 10:
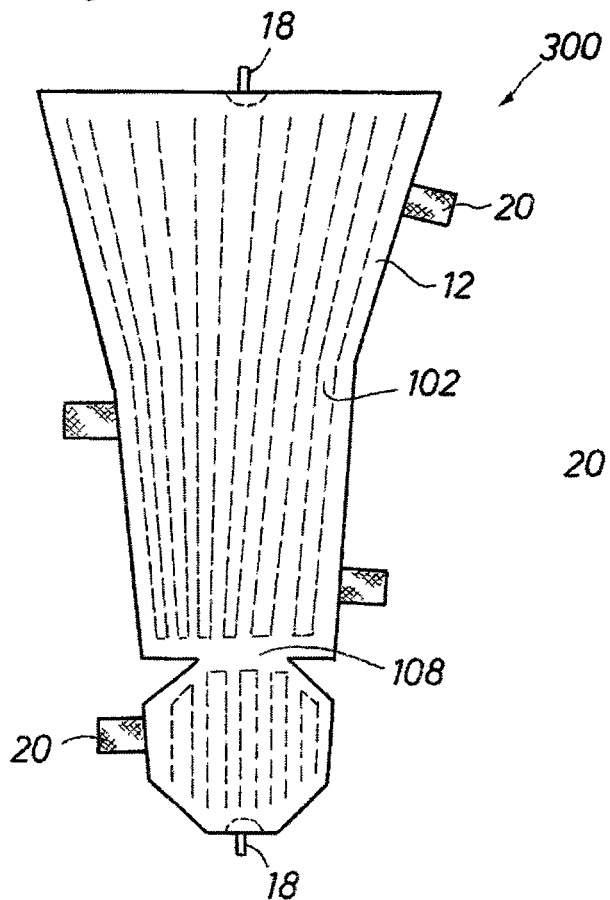
FIG. 10 is a schematic view of a lower extremity pattern casting of the present invention.
Figure 11:
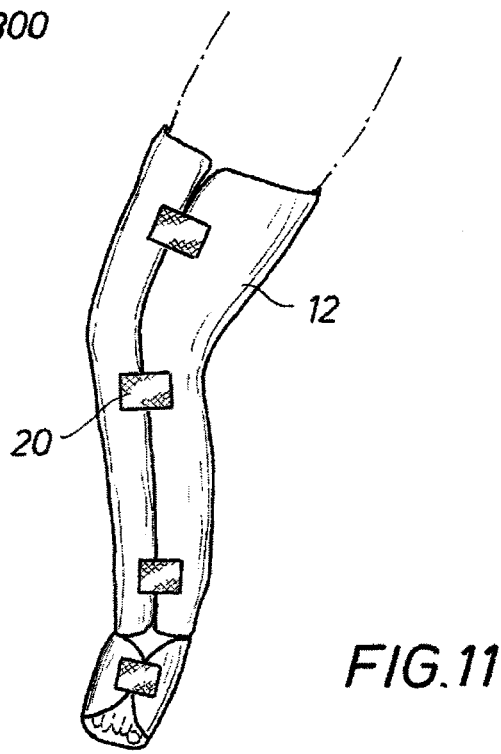
FIG. 11 is a side elevation view of the lower extremity casting of the present invention applied to the leg of a patient.
Figure 12:
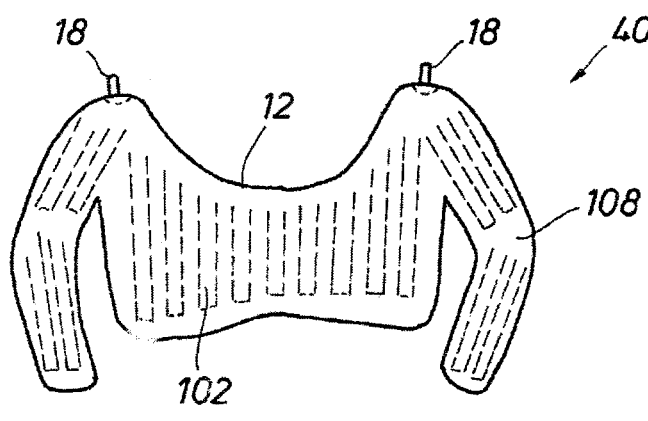
FIG. 12 is a schematic view of a shoulder spica pattern casting of the present invention.
Figure 13:
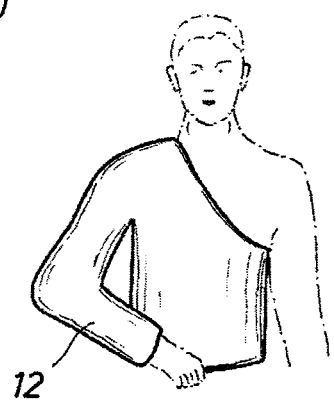
FIG. 13 is a side elevation view of the shoulder spica casting of the present invention applied to the body of a patient.

The castings of the invention may be fabricated for application to different members of a patient's body. Referring to FIGS. 8 and 9, a pantaloon hip spica pattern cast 200 is adapted for application about a patient's lower torso and upper thigh. Likewise, FIGS. 10 and 11 depict a lower extremity pattern cast 300 adapted for application about a patient's leg. In FIGS. 12 and 13, a shoulder spica pattern cast 400 is adapted for application about a patient's upper torso and arm. It will also be observed in FIGS. 6, 10 and 12 that portions 108 of the casting body 12 corresponding to the location of joints in the body member are devoid of compartments 102. The portions 108 permit the casting body 12 to have more flexibility in these areas to conveniently shape the casting body 12 to correspond to the desired orientation of the body member. For example, it may be desired that the wrist of the forearm depicted in FIG. 7 be oriented at a slight angle rather than straight.

The casting apparatus of the present invention may also be used in circumstances where use of plaster of paris or synthetic resin castings would be difficult. The casting apparatus of the present invention is portable. A suction device, such as an electric or hand operated portable suction pump, is all that is required. It may be taken camping, stored at a residence or in the truck of a vehicle in case of an accident, or in a boat, ship, aircraft or the like. The portability and light weight of the casting apparatus of the present invention is particularly suitable for use in those areas of the world, such as third world countries, where it may be easily carried with ones belonging or the like.

While a preferred embodiment of the invention has been shown and described, other and further embodiments of the invention may be devised without departing from the basic scope thereof, and the scope thereof is determined by the claims which follow.

The invention claimed is:
1. A reusable casting apparatus, comprising:
   a) a flexible casting body sealed about the perimeter thereof, said casting body defining a substantially narrow cavity; wherein said cavity includes a plurality of elongated compartments closed at one end and open at the opposite ends thereof, and wherein one or more portions of said cavity corresponding to the location of joints in the body member is devoid of said elongated compartments
   b) wherein said cavity is substantially filled with hard spherical plastic granules having a diameter of 1-2 mm;
   c) wherein said casting body includes a nozzle opening into said cavity; and
   d) means for securing said casting body about a body member.

2. The apparatus of claim 1 wherein said casting body is fabricated of airtight plastic material.

3. The apparatus of claim 1 wherein the perimeter of said casting body defines a spica pattern configured for application of said casting body about a forearm.

4. The apparatus of claim 1 wherein the perimeter of said casting body defines a spica pattern configured for application of said casting body about a lower torso and upper thigh.

5. The apparatus of claim 1 wherein the perimeter of said casting body defines a spica pattern configured for application of said casting body about a lower body extremity.

6. The apparatus of claim 1 wherein the perimeter of said casting body defines a spica pattern configured for application of said casting body about a leg.

7. The apparatus of claim 1 wherein the perimeter of said casting body defines a spica pattern configured for application of said casting body about an upper torso.

8. The apparatus of claim 1 wherein the perimeter of said casting body defines a spica pattern configured for application of said casting body about a patient's shoulder and arm.

9. A reusable casting apparatus, comprising:
 a) a pliant casting body that may be shaped to substantially conform to the contour and shape about a body member, said casting body being formed by substantially planar top and bottom members sealed about the perimeter thereof; wherein said casting body includes a plurality of elongated channels formed between said top and bottom members, said channels being closed at one end and open at the opposite ends thereof, and wherein one or more portions of said channels corresponding to the location of joints in the body member is devoid of said elongated compartments
 b) hard substantially spherical plastic beads having an average diameter of 1-2 mm substantially filling said casting body;
 c) means for securing said casting body about a body member; and
 d) said casting body including valve means for connection to a vacuum means for evacuating air from said casting body.

* * * * *